United States Patent [19]

Powell

[11] 4,434,071

[45] Feb. 28, 1984

[54] 1,3-DIBROMO DIALKYLHYDANTOIN AND OLEFIN OLIGOMER REACTION PRODUCT AS A CATALYST FOR PREPARING ALKENYL DICARBOXYLIC ACID ANHYDRIDE

[75] Inventor: Justin C. Powell, Fairfax, Va.

[73] Assignee: Texaco Inc., White Plains, N.Y.

[21] Appl. No.: 339,571

[22] Filed: Jan. 15, 1982

[51] Int. Cl.³ .................. C09K 3/00; C07D 307/60
[52] U.S. Cl. ............................ 252/182; 548/311; 549/231; 549/261
[58] Field of Search ............... 252/182; 548/311; 549/231, 261

[56] References Cited

U.S. PATENT DOCUMENTS 3,932,352 1/1976 Freedman et al. ............... 524/104
4,255,340 3/1981 Powell ........................... 549/261 X Primary Examiner—Leland A. Sebastian
Attorney, Agent, or Firm—Carl G. Ries; Robert A. Kulason; Carl G. Seutter

[57] ABSTRACT

Reaction of maleic acid anhydride and polyisobutylene is improved by use, as catalyst, of a complex of polyisobutylene and a 1,3-dibromo dialkylhydantoin.

20 Claims, No Drawings

1,3-DIBROMO DIALKYLHYDANTOIN AND OLEFIN OLIGOMER REACTION PRODUCT AS A CATALYST FOR PREPARING ALKENYL DICARBOXYLIC ACID ANHYDRIDE

FIELD OF THE INVENTION

This invention relates to novel complexes of 1,3-dibromo dialkylhydantoins. More particularly it relates to the use of such complexes as catalyst.

BACKGROUND OF THE INVENTION

Alkenyl succinic acid anhydride type compounds may be typically prepared by the reaction of a polyisobutene and maleic acid anhydride, in the presence of catalyst such as 1,3-dibromo-5,5-dialkyl hydantoin. It is found however that the reaction mixture contains undesirable sludge in amount as high as 6–7 w %.

It is an object of this invention to provide a process for preparing alkenyl succinic acid anhydrides in the presence of a novel catalyst which permits operation characterized by formation of decreased amounts of sludge. Other objects will be apparent to those skilled in the art.

STATEMENT OF THE INVENTION

In accordance with certain of its aspects, the method of this invention may comprise maintaining a mixture consisting essentially of a 1,3-dibromo dialkylhydantoin and an olefin oligomer of molecular weight $\overline{M}_n$ of 250–5000 at 150° C.–300° C. for 0.1–10 hours thereby forming a reaction mixture, and recovering said reaction mixture.

DESCRIPTION OF THE INVENTION

The unsaturated aliphatic dicarboxylic acid anhydrides which may be employed to form the desired alkenyl saturated aliphatic dicarboxylic acid anhydrides in practice of this invention may be intramolecular anhydrides typified by the following:

TABLE

| maleic | anhydride |
| citraconic | anhydride |
| itaconic | anhydride |
| ethylmaleic | anhydride |
| halo(eg chloro)maleic | anhydride, etc. |

The preferred anhydride is maleic anhydride.

The olefin oligomer, or polyolefin, reactant which may be employed may typically be an oligomer of a $C_2$–$C_8$ olefin having a molecular weight $\overline{M}_n$ of about 250–30,000, more commonly about 300–3000, say 1000–1400. The preferred oligomers are the polyisobutylenes, more preferably polyisobutylene of $\overline{M}_n$ of 300–3000.

The polybutenes which may be employed may include those polymers obtained by polymerizing refinery streams containing eg isobutylenes, cis-butene-2,trans-butene-2, and butene-1. Polymerization of such streams, typically by use of a Friedel-Crafts catalyst, permits attainment of a polyisobutylene of $\overline{M}_n$ of 250–3000, preferably 500–2000, say 700–1500, typically 1050–1400, and a viscosity of 4000–5500 centistokes at 100° C. Molecular weight $M_n$ may be determined by ASTM D-2503 method.

Reaction between the polyolefin and the unsaturated aliphatic dicarboxylic acid anhydride to form the desired product alkenyl saturated aliphatic dicarboxylic acid anhydride may be carried out at 150° C.–300° C. preferably about 210° C.–245° C., say about 245° C. for 2–10, preferably 4–10, say 6 hours at autogenous pressure in batch operation or at 150° C.–300° C., preferably 210° C.–245° C., say about 245° C. for 1–3 hours in a continuous process.

It is a feature of the novel process of this invention that it be carried out in the presence of a catalyst complex prepared by reacting an olefin oligomer and a 1,3-dibromo dialkylhydantoin.

The olefin oligomer or polyolefin which may be employed to form the catalyst complex of this invention may be selected from the same group as that from which the olefin oligomer or polyolefin reactant supra is selected. This may include polymers of:

TABLE ethylene
propylene
isobutylene
cis-butene-2
trans-butene-2
butene-1
isoamylenes
hexenes etc.

The preferred olefin oligomer or polyolefin which is used to form the catalyst complex may be polyisobutylene; and preferably the same olefin as is used as the reactant to prepare the alkenyl saturated aliphatic dicarboxylic acid anhydride.

The typically $C_2$–$C_8$ oligomer may have a molecular weight $\overline{M}_n$ of about 250–30,000, more commonly about 300–3000, say 1000–1400. A preferred composition may be the Indopol H-300 polyisobutylene of molecular weight $\overline{M}_n$ of 1050–1400, say about 1290.

The 1,3-dibromo dialkylhydantoin which may be employed to form the novel catalyst complex of this invention may include 1,3-dibromo-5,5-dialkylhydantoins, preferably those bearing $C_1$–$C_{10}$ alkyl groups. Typical of the alkyl groups may be:

TABLE methyl
ethyl
propyls
butyls
amyls
hexyls
octyls
decyls
octadecyls etc.

The preferred hydantoin is 1,3-dibromo-5,5-dimethylhydantoin.

The catalyst complex of this invention may be prepared by reacting one mole of the 1,3-dibromo dialkylhydantoin compound with 1–2000 moles, say 1000 moles of the olefin oligomer. Reaction may be effected by maintaining the mixture at 150° C.–300° C., preferably 200° C.–280° C., say 245° C. for 0.1–10 hours, say about 6 hours. During the course of the reaction, the hydantoin, typically 1,3-dibromo-5,5-dimethylhydantoin (D), reacts with the olefin oligomer (G) to form a complex.

D·nG wherein D represents the hydantoin derived moiety; and G represents the olefin oligomer derived moiety, and n represents a small integer 1–3, typically 1.

It is preferred to carry out the reaction between the hydantoin and the olefin in an excess of olefin. Thus in this preferred embodiment, the olefin may be present in amount of 1–2000 moles, preferably 1000–1500 moles, say 1000 moles per mole of hydantoin. The complex D·nG will then be formed in an excess of the olefin oligomer and in normal operation it will not be isolated as pure complex but will be used in solution in the olefin as prepared.

It is a feature of this invention that it be carried out in the substantial absence of the unsaturated aliphatic dicarboxylic acid anhydride which is a component of the reaction in which the instant complex may be used as catalyst. Although small amounts of unsaturated anhydrides e.g. maleic anhydride may be present during the reaction in which the complex is formed, there is no particular advantage which arises from presence of this component; and preferred operation is carried out in the presence of less than 0.10 mole of the anhydride per mole of the hydantoin compound. Most preferably no unsaturated aliphatic dicarboxylic acid anhydride is added to or is present during the reaction in which the complex is formed.

The molar ratios supra of olefin to hydantoin compound used to form the complex may be expressed in terms of parts per million. It is found that 20–150,000 ppm,. say 90–100 ppm of the hydantoin compound may be added to the olefin oligomer.

Illustrative complexes D·nG in excess of G may be those wherein D is:

TABLE 1,3-dibromo-5,5-dimethyl hydantoin
1,3-dibromo-5,5-diethyl hydantoin
1,3-dibromo-5,5-di-n-propyl hydantoin
1,3-dibromo-5,5-di-isopropyl hydantoin
1,3-dibromo-5,5-di-cyclohexyl hydantoin and wherein G is:

TABLE

| olefin oligomer | $\overline{M}_n$ |
| --- | --- |
| polyisobutylene | 1000–1400 |
| polyisobutylene | 1200 |
| polyethylene | 1000–2000 |
| polypropylene | 1000–2000 |

One preferred complex is the complex (1:1 molar).1,3-dibromo-5,5-dimethyl hydantoin.polyisobutylene ($\overline{M}_n$ 1290)

The exact nature or chemical composition of the complex is not known. Analysis of the mixture of complex in the excess of e.g. polyisobutylene in which it may be prepared reveals that at low concentrations of hydantoin compound (e.g. 90 ppm) the polyisobutylene is not found to be measurably different from the starting olefin. At higher concentrations such as 111,000 ppm (i.e. 11.1 w %) (which is equivalent to one gram atom per mole of olefin oligomer) the system changes from light colored to dark colored. Chromatography indicates a decrease of about 2 w % in the amount of underivatized polyisobutylene. Spectroscopic analysis reveals a shift in the olefin isomers which are present. NMR indicates a possible small increase in unsaturation and there is some evidence of a terminal bromovinylidene structure on the olefin. NMR and IR analyses show a marked decrease of trialkyl substituted alkene isomers.

In the preferred embodiment, the complex may be used in the mixture in which it is formed with no further treatment, purification, or recovery. The amount of catalyst complex which may be employed in the reaction of polyolefin and unsaturated aliphatic dicarboxylic acid anhydride may be 0.0001–1.0 moles, preferably 0.0005–0.0020 moles, say 0.0010 moles (of hydantoin compound from which it was formed) per mole of unsaturated dicarboxylic acid anhydride reacted. In typical operation, this may be equivalent to 0.005–0.02 parts, preferably 0.006–0.001 parts of complex (as formed in solution in excess of olefin) per 100 parts of acid anhydride.

It may be desirable to adjust the stoichiometry of the olefin-anhydride reaction by allowing for the olefin present in the catalyst complex; normally this may be such a small amount however that it may not be necessary.

Thus there may be added to the reaction medium in which the alkenyl aliphatic dicarboxylic anhydride is to be prepared, the following parts of the several components per mole of olefin:

TABLE

| Component | Broad | Preferred | Typical |
| --- | --- | --- | --- |
| anhydride (moles) | 0.5–5 | 0.8–2 | 1.1–1.5 |
| catalyst complex (ppm*) | 20–2000 | 50–150 | 60–100 |

*by weight of total olefin

It will be found that the reaction (using the catalyst complex to prepare the alkenyl saturated dicarboxylic acid anhydride) proceeds with formation of sludge in amounts which are substantially less than would be the case if the catalyst were an uncomplexed hydantoin. In the latter case, sludge may be observed typically in amounts greater than 1 w % (based on total weight of reactants) and up to as high as 6–7 w %. Use of the catalyst complex of this invention permits attainment of reaction mixture containing generally less than about 1 w % sludge as determined by The Sludge Determination Test which includes dissolving the crude product (after stripping in vacuo to remove the bulk of the unreacted unsaturated dicarboxylic acid anhydride) in petroleum ether and filtering through diatomaceous earth. The insoluble residues are washed further with hexane and chloroform; and then acetone is used to dissolve both the the residues adhering to the reactor walls and the insoluble residues on the filter cake. The combined acetone solutions are stripped at 130° C. for one hour at 5 mm Hg. The residue is calculated in percentage of the sum of the original reactants charged.

In one pair of examples conducted under comparative conditions, the sludge is reduced from e.g. 15 w % to 0.84 w %, while the yield of desired derivatived polyisobutylene is increased.

It will thus be seen that the use of the catalyst complex permits attainment of several advantages:

(i) attainment of increased yield of desired product;

(ii) attainment of reaction mixture having decreased sludge content;

(iii) greater ease of handling of somewhat larger volume of catalyst complex which includes carrier material e.g. decreased probability of errors in catalyst dosage etc.

(iv) elimination of need for activation prior to use as is true of some prior art catalysts; and (v) avoidance of by-products arising from reaction of 1,3-dibromo dialkylhydantoin with the second reactant, unsaturated aliphatic dicarboxylic acid, and thereby increasing the yield of desired product.

The product, typically alkenyl succinic acid anhydride, prepared by the process of this invention may be used as additive to a hydrocarbon such as a motor fuel (to provide increased rust inhibition and carburetor detergency) or a lubricating oil (to provide rust inhibition) etc.

DESCRIPTION OF PREFERRED EMBODIMENTS

Practice of the process of this invention will be apparent to those skilled in the art from the following examples wherein, as elsewhere in this specification, all parts are parts by weight unless otherwise stated.

EXAMPLE I

In this example which shows a preferred embodiment for carrying out the process of this invention, a catalyst complex may be prepared by adding 100 parts of Indopol H-300 brand of polyisobutylene ($\overline{M}_n$ of 1290) to a reaction vessel. There may be added 0.055 parts of 1,3-dibromo-5,5-dimethyl hydantoin corresponding to 5500 ppm based on the polyisobutylene. The reaction vessel is sealed and the mixture heated to 245° C. at autogenous pressure for 6 hours with agitation. At the end of the reaction time, the mixture is found to have changed from a light straw color to a dark brown color. During the course of the reaction, there is formed the catalyst complex corresponding to 1,3-dibromo-5,5-dimethylhydantoin.polyisobutylene ($\overline{M}_n$ of 1290) in an excess of polyisobutylene ($\overline{M}_n$ of 1290).

Preparation of polyisobutenyl ($M_n$ of 1290) succinic acid anhydride is effected by adding to a reaction vessel 98.4 parts (0.077 moles) of H-300 polyisobutylene ($M_n$ of 1290) and 8.33 parts (0.085 moles) of maleic acid anhydride. To this mixture there is added 1.6 parts of the catalyst complex above-prepared. This corresponds to 90 ppm of 1,3-dibromo-5,5-dimethyl hydantoin equivalent based upon charge polyisobutylene. For calculation of these ratios, credit is taken for the parts of polyisobutylene added to the reaction vessel plus the parts of polyisobutylene used to prepare the catalyst complex (which latter includes approximately 95 parts which are the solvent in which the actual complex is formed).

Reaction is carried out at 245° C. and autogenous pressure for 2 hours with agitation. During the course of the typical reaction, polyisobutylene and maleic acid anhydride react in the presence of the polyisobutylene-hydantoin catalyst complex to form desired product polyisobutenyl succinic acid anhydride in yield approaching 60% of stoichiometric.

The product is found to contain sludge in decreased amount of about 0.63 w % based on total reactants as analyzed by The Sludge Determination Test supra.

The product is useful as a carburetor detergent additive in manner similar to that in which comparable products have heretofore been employed.

EXAMPLE II

In this Example, a series of Runs is carried out to determine the effect of various treatments on a charge olefin - the Indopol H-300 brand of polyisobutylene ($\overline{M}_n$ of 1290). In the table which follows, there are tabulated for various specimens, the following:

(i) DB Conc ppm—the parts per million of 1,3-dibromo-5,5-dimethyl 1 hydantoin added;

(ii) Color—as determined by visual inspection;

(iii) % Br—weight % bromine in the final reaction product;

(iv) % C and % H—weight % carbon and hydrogen in the final reaction product;

(v) % PIB—weight % of polyisobutylene as determined by chromatography;

(vi) OIA—olefin isomer analysis: trialkyl substituted olefinic carbon double bonds/dialkyl substituted olefin carbon double bonds, determined by NMR (adjusted peak area ratios);

(vii) Ratio—the fraction of (vi) calculated as a weight ratio;

(viii) IR Ratio—the ratio of trialkyl substituted olefin carbon double bonds to dialkyl substituted olefinic carbon double bonds as determined by infra-red absorption spectroscopy (as adsorbance ratio);

(ix) MW—molecular weight $\overline{M}_n$.

In the Table, Column A lists the specification values for the Indopol H-300 brand of polyisobutylene;

Column B lists values actually measured of the polmisobutylene;

Column C lists the values measured after the charge polyisobutylene is heated at 245° C.-for 6 hours;

Column D lists the values measured after addition of 0.009 parts of 1,3-dibromo-5,5-dimethyl hydantoin to 100 parts of polyisobutylene (corresponding to 90 ppm) followed by heating at 245° C. for 6 hours;

Column E lists the values measured after addition of 11 parts of 1,3-dibromo-5,5-dimethyl hydantoin to 100 parts of polyisobutylene (corresponding to 110,000 ppm) followed by heating at 245° C. for 6 hours;

Column F list theoretical calculated values for the bromopolybutene reaction product which may be formed in the reaction steps of columns D and E.

TABLE

|  | A | B | C | D | E | F |
|---|---|---|---|---|---|---|
| DB Conc ppm | — | — | 0 | .90 | 110,000 | — |
| Color | Nil | Nil | Nil | Nil | V. Dark | — |
| % Br | — | — | — | — | 0.32 | 5.8 |
| % C | 85.6 | — | — | — | 85.4 | 80.6 |
| % H | 14.4 | — | — | — | 14.2 | 13.5 |
| % PIB | — | 97.9 | 98.6 | 98.7 | 96.2 96.4 | — |
| OIA | — | 37/8 45/8 | 39/6 | 46/12 | 30/10 | — |
| Ratio | — | 4.6 5.6 | 6.5 | 3.8 | 3.8 | — |
| IR Ratio | — | 0.54 | 0.42 | 0.30 | * | — |
| MW | 1290 | 1310 1260 | 1260 | 1420 | 1320 | 1370 |

*species is reduced but not absent.

Inspection of the above table reveals that the charge polyisobutylene when heated at 245° C. for 6 hours (Column C) is not significantly changed from the unheated charge of Columns A and B. Addition of 90 ppm of the hydantoin compound (Column D) shows only slight changes over Column C. The product of Column E is very dark and only 5.5% of the bromine added is found on analysis.

EXAMPLES III-XVII

In this series of Examples, H-300 brand of polyisobutylene and maleic acid anhydride are reacted together in a particular mole ratio (MR) at 216° C. or 245° C. for various reaction times as set forth in the Table which follows. In control Examples VIII and XIV–XV, no additive is present. In control Examples VI–VII, IX, XI, and XVI–XVII, there is present as additive 1,3-dibromo-5,5-dimethyl hydantoin in the concentration set forth. In control Example X, and XII–XIII, there is present a commercial anti-oxidant. In Experimental Examples III–V, the additive is the complex of polyisobutylene (PIB) and hydantoin compound (DB) prepared in Example I supra.

In each case, at the end of the reaction period, there is determined the weight of sludge and the percent of derivatized polyisobutylene (DPIB). The latter is a measure of the degree of reaction. Generally the most satisfactory runs are those which give a low sludge content together with a high DPIB.

TABLE

| Example | Additive[1] | Conc.[2] | MR[3] | °C. | Hr. | Sludge[4] wt % | DPIB % |
|---------|-------------|----------|-------|-----|-----|----------------|--------|
| III | PIB-DB | 5500 | 1.1 | 216 | 6.0 | — | 49.8 |
| IV | PIB-DB | 5500 | 1.1 | 216 | 10.0 | 0.84 | 58.6 |
| V | PIB-DB | 5500 | 1.1 | 245 | 2.0 | 0.63 | 58.8 |
| VI | DB | 100 | 1.1 | 216 | 6.0 | 1.5 | 36.8 |
| VII | DB | 90 | 1.1 | 216 | 10.0 | 1.5 | 56.4 |
| VIII | — | — | 2.0 | 216 | 10.0 | 2.1 | 58.7 |
| IX | DB | 100 | 2.0 | 216 | 10.0 | 6.7 | 61.0 |
| X | AO | 6585 | 2.0 | 216 | 10.0 | 2.6 | 61.9 |
| XI | DB | 90 | 2.0 | 245 | 6.0 | 4.3 | 73.5 |
| XII | AO | 3621 | 1.1 | 245 | 6.0 | 1.3 | 58.6 |
| XIII | AO | 3621 | 1.1 | 245 | 6.0 | 1.3 | 60.3 |
| XIV | — | — | 1.1 | 245 | 6.0 | 1.4 | 57.1 |
| XV | — | — | 1.1 | 245 | 6.0 | 1.3 | 58.5 |
| XVI | DB | 90 | 1.1 | 245 | 6.0 | 0.77 | 68.0 |
| XVII | DB | 90 | 1.1 | 245 | 2.25 | — | 59.1 |

[1]AO is antioxidant Ethyl AN-702, brand of 4,4'-methylene-bis-(2,6-di-t-butyl phenol)
[2]Conc. is ppm weight based on H-300
[3]Mole ratio, MAA to PIB
[4]Based on reactants.

From the above table, it will be apparent that the novel complex permits attainment of results which are better than those of the control examples. By way of illustration, use of the complex of this invention gives in Example IV, a 44% reduction in sludge over the use of the uncomplexed hydantoin compound in Example VII.

It should be noted that Example IV is merely the continuation of Example III. Sludge could not be determined for Example III directly, but it is certain to be less than for Example IV because it is known that sludge increases with reaction time in the 0 to 10 hr range.

It should also be noted that the derivatized polyisobutylene DPIB is maintained desirably high at 49.8%–58.8% while that of the control Examples may drop to as low as 36.8% with substantially higher sludge content.

A comparison of Example III with Example VI shows the temperature activation effect. It is believed that the higher conversion to desired product (represented by % DPIB) and lower conversion to sludge (Sludge wt %) is the result of prior thermal activation of the olefin hydantoin compound (DB) complex which has taken place in the course of its preparation. The complex does not appear to promote sludge formation as strongly as does DB alone.

Although this invention has been illustrated by reference to specific embodiments, it will be apparent to those skilled in the art that various changes and modifications may be made which clearly fall within the scope of this invention.

I claim:

1. The method which comprises
   maintaining a mixture consisting essentially of a 1,3-dibromo dialkylhydantoin and an olefin oligomer of molecular weight $\overline{M}_n$ of 250–30,000 at 150° C.–300° C. for 0.1–10 hours thereby forming a reaction mixture; and
   recovering said reaction mixture.

2. The method claimed in claim 1 wherein said 1,3-dibromo dialkylhydantoin is 1,3-dibromo-5,5-dialkyl hydantoin.

3. The method claimed in claim 1 wherein said 1,3-dibromo dialkyl hydantoin is 1,3-dibromo-5,5-dimethyl hydantoin.

4. The method claimed in claim 1 wherein said olefin oligomer is a polypropylene.

5. The method claimed in claim 1 wherein said olefin oligomer is a polyisobutylene.

6. The method claimed in claim 1 wherein the said olefin oligomer is present in the complex in amount of 5–1000 parts per part of 1,3-dibromo dialkylhydantoin.

7. The method claimed in claim 1 wherein said olefin oligomer is present in excess of 1,3-dibromo dialkylhydantoin.

8. The method which comprises
   maintaining a mixture consisting essentially of a 1,3-dibromo dimethyl hydantoin and a polyisobutylene of molecular weight $\overline{M}_n$ of 250–30,000 at 200° C.–280° C. for 0.1–10 hours thereby forming a reaction mixture; and
   recovering said reaction mixture.

9. The reaction product of a 1,3-dibromo dialkylhydantoin and an olefin oligomer of molecular weight $M_n$ of 250–30,000.

10. The reaction product claimed in claim 9 wherein said bromo dialkylhydantoin is 1,3-dibromo-5,5-dialkyl hydantoin.

11. The reaction product claimed in claim 9 wherein said bromo dialkylhydantoin is 1,3-dibromo-5,5-dimethyl hydantoin.

12. The reaction product claimed in claim 9 wherein said olefin oligomer is a polybutylene.

13. The reaction product claimed in claim 9 wherein said olefin oligomer is a polyisobutylene of molecular weight $\overline{M}_n$ of 1050–1400.

14. The reaction product of one part of a brominated dialkylhydantoin and 5000–50,000 parts of a olefin oligomer of molecular weight $M_n$ of 250–5000.

15. The reaction product of 1,3-dibromo-5,5-dimethyl hydantoin and a polyisobutylene of molecular weight $M_n$ of 1050–1400 in an excess of polyisobutylene.

16. The method of preparing a product alkenyl aliphatic dicarboxylic acid anhydride which comprises reacting at 150° C.–300° C.
   (i) an olefin oligomer reactant of molecular weight $\overline{M}_n$ of 250–30,000;
   (ii) an unsaturated aliphatic dicarboxylic acid anhydride in amount of 0.5–5 moles per mole of olefin oligomer;
   and
   (iii) as catalyst, 0.5 w %-50 w %, based on said olefin reactant of the reaction product of a 1,3-dibromo dialkylhydantoin and an excess of an olefin oligomer of molecular weight $\overline{M}_n$ of 250–30,000 thereby forming product alkenyl aliphatic decarboxylic acid anhydride; and recovering said product alkenyl aliphatic dicarboxylic acid anhydride.

17. The method of preparing a product as claimed in claim 16 wherein said unsaturated aliphatic dicarboxylic acid anhydride is maleic acid anhydride.

18. The method of preparing a product as claimed in claim 16 wherein said olefin oligomer reactant is a polyisobutylene.

19. The method of preparing a product as claimed in claim 16 wherein the olefin oligomer reactant is the same as the olefin oligomer reacted with said 1,3-dibromo dialkylhydantoin.

20. The method of preparing an isobutenyl succinic acid anhydride which comprises reacting at 150° C.–300° C.;
(i) a polyisobutylene of molecular weight $\overline{M}_n$ of 250–5000;
(ii) maleic anhydride in amount of 0.8–5 moles per mole of polyisobutylene reactant; and
(iii) as catalyst, 0.5 w %–50 w %, based on said polyisobutylene reactant, of the reaction product of 1,3-dibromo-5,5-dimethyl hydantoin and polyisobutylene of molecular weight $\overline{M}_n$ of 250–5000 thereby forming product polybutenyl succinic acid anhydride; and
recovering said product polybutenyl succinic acid anhydride.

* * * * *